United States Patent [19]

Sawayanagi et al.

[11] Patent Number: 5,482,973
[45] Date of Patent: Jan. 9, 1996

[54] SUPPOSITORY PREPARATION

[75] Inventors: Yoichi Sawayanagi, Tokyo; Yutaka Kawamura, Narita, both of Japan

[73] Assignee: Dojin Iyaku-Kako Co., Ltd., Tokyo, Japan

[21] Appl. No.: 136,616

[22] Filed: Oct. 15, 1993

Related U.S. Application Data

[63] Continuation of Ser. No. 885,351, May 19, 1992, abandoned.

[30] Foreign Application Priority Data

May 24, 1991 [JP] Japan .................................. 3-120019

[51] Int. Cl.$^6$ .......................... A61K 31/19; A61K 31/22; A61K 31/225
[52] U.S. Cl. .......................... 514/570; 514/546; 514/547; 514/549; 424/DIG. 15
[58] Field of Search .................................. 514/570, 546, 514/547, 549; 424/DIG. 15

[56] References Cited

U.S. PATENT DOCUMENTS 3,931,205  1/1976  Nakanishi et al. .................. 546/89
4,456,759  7/1984  Muchowski et al. ............... 548/453
4,698,359  10/1987  Niederer et al. .................. 424/DIG. 15

FOREIGN PATENT DOCUMENTS

WO84/00490  2/1984  WIPO.

OTHER PUBLICATIONS

The Merck Index, 10th Ed. p. 1381, abstract No. 9476 (1983).
World Patents Index Latest, No. 91104770, & JP-A-3-041-020, Feb. 21, 1991, "Release Control Pharmaceutical Composition Mucous Membrane Preparation Freeze Viscosity Emulsion Fatty Acid Alcohol PVA Cation Medicine Water".

Primary Examiner—Zohreh Fay
Assistant Examiner—K. Weddington
Attorney, Agent, or Firm—Oblon, Spivak, McClelland, Maier & Neustadt

[57] ABSTRACT

A suppository comprising pranoprofen is disclosed. The suppository has analgesic or anti-inflammatory effects. Since pranoprofen is administered away from gastrointestinal tracts, application of the suppository is not accompanied by side effects such as peptic ulcer, bleeding in constipation, and diarrhea. It is particularly suitable for patients with disorders in digestive organs and infant patients. Pranoprofen is released constantly over a extended period of time.

4 Claims, 1 Drawing Sheet

SUPPOSITORY PREPARATION

This is a continuation of application Ser. No. 07/885,351, filed May 19, 1992, now abandoned.

BACKGROUND OF THE INVENTION

1. Field of the Invention

The present invention relates to a suppository preparation, and, more particularly, to an analgesic, anti-inflammatory suppository preparation comprising pranoprofen.

2. Description of the Background

Pranoprofen is popularly used in clinics in forms such as tablets, capsules, and the like as a non-steroidal anti-inflammatory and analgesic drug due to its excellent anti-inflammatory and analgesic activity.

Since non-steroidal anti-inflammatory and analgesic drugs usually exhibit side effects less strong than steroidal drugs, they are more widely used in clinics. However, oral administration of non-steroidal anti-inflammatory and analgesic drugs frequently causes side effects such as peptic ulcer and the like. Especially, oral administration to patients with disorders in digestive organs and infant patients is sometimes difficult. Because of this, suppositories of indomethacin and sodium diclofenac have been developed in order to alleviate such side effects in digestive tracts due to oral administration or to treat patients to whom no drugs can be orally dosed. These suppositories, however, are reported to exhibit serious side effects such as shocks in elderly patients, infant, or brokendown patients.

SUMMARY OF THE INVENTION

The present inventors have undertaken extensive studies in order to develop a safe, analgesic or anti-inflammatory suppository preparation which can exhibit the same degree of effects as drugs for oral administration without side effects. The present inventors focussed their research activities on pranoprofen which is safer and has weaker side effects than other non-steroidal anti-inflammatory and analgesic drugs. As a result, the inventors were successful in developing a pranoprofen suppository preparation exhibiting concentration changes in blood equivalent to the case where a pranoprofen preparation for oral administration was dosed.

Accordingly, an object of the present invention is to provide a suppository comprising pranoprofen.

Other objects, features and advantages of the invention will hereinafter become more readily apparent from the following description.

DETAILED DESCRIPTION OF THE INVENTION AND PREFERRED EMBODIMENTS

Figure 1:
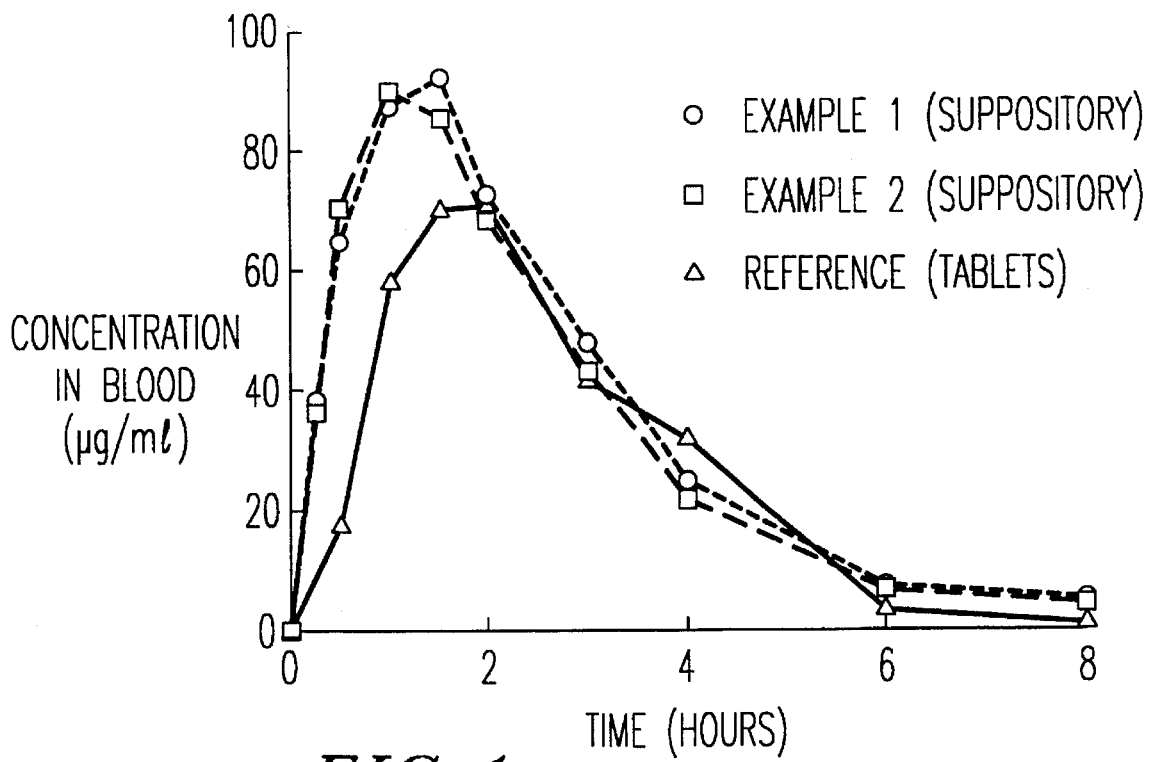
FIG. 1 is a drawing showing changes in the concentration of pranoprofen in blood after pranoprofen was administered by suppository to rabbits according to Test Example 1.

A concentration of pranoprofen in the suppository of the present invention may be in a range in which the effects of pranoprofen are exhibited. The concentration should be suitably adjusted depending on ages and symptoms of the patients. A desirable content in a suppository is usually in a range of 25–225 mg.

Any base components commonly used for suppositories can be used as a base component of the suppository of the present invention, including oils and fats, waxes, and the like of animal, vegetable or mineral origins. They may be partially or totally synthesized materials.

Specific examples given of oils and fats are olive oil, corn oil, castor oil, cottonseed oil, wheat germ oil, cacao oil, hydrogenated oils, etc.; of hydrocarbons are squalan, petrolatum, solid paraffin, liquid paraffin, etc.; and of waxes are jojoba oil, carnauba wax, bees wax, lanolin, etc. As partially or totally synthesized esters of glycerol fatty acid, mono-, di-, or triglycerides of medium or higher fatty acid, such as saturated linear fatty acid, e.g., lauric acid, myristic acid, palmitic acid, stearic acid, etc., or unsaturated linear fatty acid, e.g., oleic acid, linoleic acid, linolenic acid, etc, are given. Commercial products which can be used as a base of the suppository of the present invention include Witebsol (trademark, a fatty acid triglyceride product of Dynamit Nobel), Pharmasol (trademark, a fatty acid triglyceride product of Nippon Oil and Fats Co.), Isocacao (trademark, a fatty acid triglyceride product of Kao Corp.), SB (trademark, a fatty acid triglyceride product of Taiyo Oil and Fats Co.), Novata (trademark, a fatty acid triglyceride product of Henkel), Suppocire (trademark, a fatty acid triglyceride product of Gattefosse Co.), and the like. Polyethylene glycol, e.g., macrogole, setomacrogole, etc., as well as derivatives thereof, are given as examples of other synthetic products.

Other additives such as preservatives, stabilizers, surfactants, perfumes, pigments, pH modifiers, purified water, and the like may be optionally added to the suppository of the present invention.

The suppository of the present invention can be prepared by adding pranoprofen and other optional components, e.g., a pH modifier, to a base component and molding the mixture into solid suppositories. Alternatively, it can be made into the form of suppositories encapsuled by soft gelatin or of rectal injection type ointments.

According to the present invention a non-steroidal type analgesic or anti-inflammatory suppository which exhibites a concentration change in blood equivalent to oral preparations can be provided.

Other features of the invention will become apparent in the course of the following description of the exemplary embodiments which are given for illustration of the invention and are not intended to be limiting thereof.

EXAMPLES

Example 1

11,250 mg of Witebsol H15 (trademark, a product of Dynamit Novel) was molten at 60° C. to dissolve 750 mg of pranoprofen therein. After cooling to 40° C., the mixture was stirred to homogenize and filled in containers to obtain 10 suppositories, each weighing 1.2 g and containing 75 mg of pranoprofen.

Example 2

11,250 mg of polyethylene glycol 1540 (trademark, a product of Nippon Oil and Fats Co.) was molten at 80° C. to dissolve 750 mg of pranoprofen therein. After cooling to 40° C., the mixture was stirred to homogenize and filled in containers to obtain 10 suppositories, each weighing 1.2 g and containing 75 mg of pranoprofen.

Example 3

7.5 g of pranoprofen was dispersed into purified water and 3 g of Highvis Wako 104 (trademark, a fatty acid triglyceride manufactured by Wako Pure Chemicals Co.) was added to the dispersion. After stirring to homogenize, triethanolamine was added in an amount to make the mixture pH 7.0, followed by the addition of purified water in an amount appropriate to make 100 g of a transparent gel with stirring. The gel was filled in 2.5 cc disposable syringes to obtain 50 pieces of syringed pranoprofen injection preparation, each weighing 2 g and containing 150 mg of pranoprofen.

Example 4

1.5 g of hydroxypropyl cellulose (HPCH: trademark, manufactured by Nippon Soda Co.) and 1,250 mg of pranoprofen were dispersed in 47.25 g of warmed purified water and stirred to homogenize. Stirring was continued while cooling the mixture to 10° C. thus obtaining a gel preparation. The gel was filled in 1.5 cc disposable syringes to obtain 50 pieces of syringed pranoprofen injection preparation, each weighing 1 g and containing 25 mg of pranoprofen.

Example 5

14 g of Witebsol W35 (trademark, a product of Dynamit Novel) was molten at 60° C. After cooling to 40° C., 1 g of pranoprofen was dissolved. The mixture was stirred to homogenize and filled in containers to obtain 20 suppositories, each weighing 0.75 g and containing 50 mg of pranoprofen.

Example 6

2.7 g of polyethylene glycol 4000 (trademark, a product of Nippon Oil and Fats Co.) and 2.7 g of polyethylene glycol 1000 (trademark, a product of Nippon Oil and Fats Co.) were molten at 80° C. to dissolve 1.5 g of pranoprofen therein. After cooling to 40° C., the mixture was filled in containers to obtain 10 suppositories, each weighing 1.5 g and containing 150 mg of pranoprofen.

Example 7

10 g of pranoprofen was dispersed into 90 g of triglyceride of medium chain fatty acid (Panasate 810: trademark, a product of Nippon Oil and Fats Co.) and the mixture was stirred to homogenize. The mixture was filled in capsules, 1 g per capsule, to obtain 100 pranoprofen rectal capsules, each containing 100 mg of pranoprofen.

Test Example 1

Suppositories prepared in Examples 1 and 2 were rectally administered to 3 rabbits (Japanese White Oryctolagus, weight: 2.5 kg), one suppository to each rabbit, to observe changes in pranoprofen concentrations in blood. As a control, a tablet containing the same amount (75 mg) of pranoprofen was orally administered to 3 rabbits. 2 cc of blood was sampled from ear vein of each rabbit before the administration and at 0.25, 0.5, 1, 1.5, 2, 3, 4, 6, and 8 hours after the administration to measure pranoprofen concentrations in blood. The results are shown in FIG. 1.

Test Example 2

Figure 2:
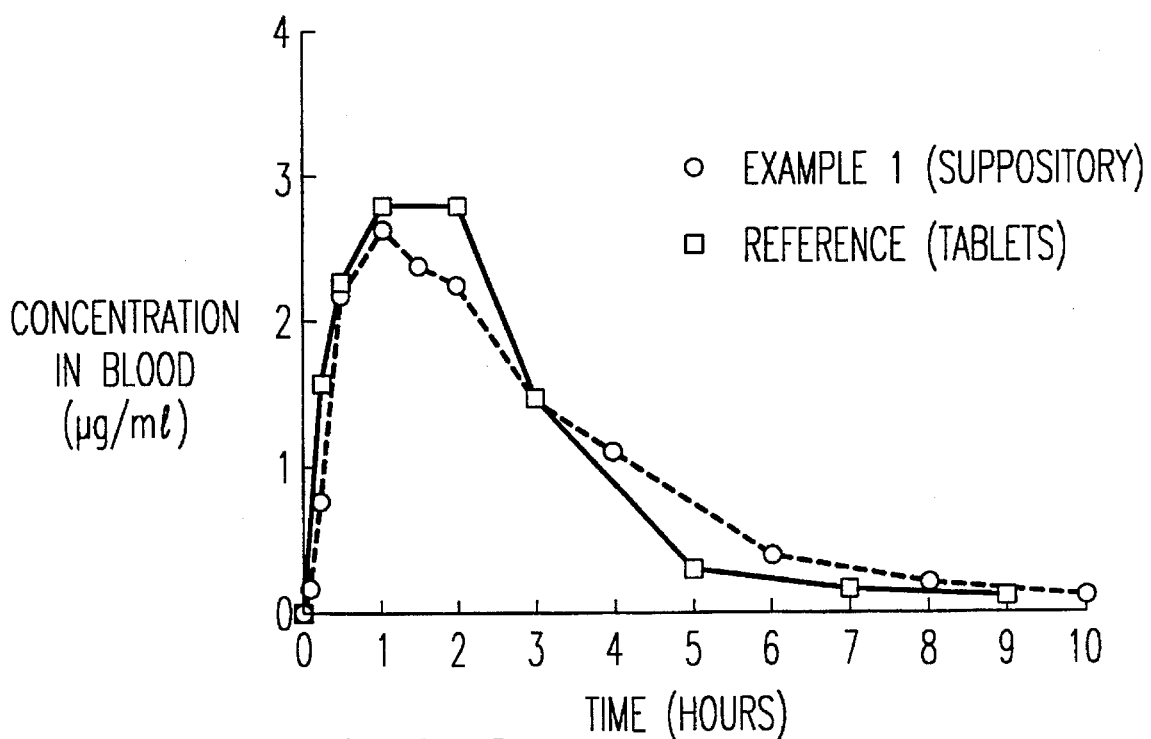
FIG. 2 is a drawing showing changes in the concentration of pranoprofen in blood after pranoprofen was administered by suppository to healthy persons according to Test Example 2.

Suppositories prepared in Examples 1 were rectally administered to 3 healthy persons, one suppository to each person, to observe changes in pranoprofen concentrations in blood. Blood was sampled from the vein of fore arm before the administration and at 0.125, 0.25, 0.5, 1, 1.5, 2, 3, 4, 6, 8, and 10 hours after the administration to measure pranoprofen concentrations in blood by HPLC. The results are shown in FIG. 2, together with data taken from literature showing the change in pranoprofen concentration in blood in healthy persons who were orally administered 75 mg of pranoprofen by tablets.

Obviously, numerous modifications and variations of the present invention are possible in light of the above teachings. It is therefore to be understood that within the scope of the appended claims, the invention may be practiced otherwise than as specifically described herein.

What is claimed is:

1. A suppository preparation consisting essentially of pranoprofen and a base component, wherein the pranoprofen concentration is 2.5–10% by weight and is present in an amount of 25–225 mg per one suppository, said base component selected from the group consisting of fatty acid monoglyceride, fatty acid diglyceride, fatty acid triglyceride, polyethylene glycol and mixtures thereof.

2. The suppository of claim 1 consisting essentially of pranoprofen and a fatty acid triglyceride.

3. A suppository preparation consisting essentially of pranoprofen and a base component, wherein the pranoprofen concentration is 2.5–10% by weight and is present in an amount of 25–225 mg per one suppository, said base component selected from the group consisting of fatty acid monoglyceride, fatty acid diglyceride, fatty acid triglyceride, polyethylene glycol and mixtures thereof, water and a pH modifier.

4. The suppository of claim 3 wherein the pH modifier is triethanolamine.

\* \* \* \* \*